US006496705B1

(12) United States Patent
Ng et al.

(10) Patent No.: US 6,496,705 B1
(45) Date of Patent: Dec. 17, 2002

(54) PROGRAMMABLE WIRELESS ELECTRODE SYSTEM FOR MEDICAL MONITORING

(75) Inventors: Richard Ng, Cary, IL (US); Salvador Lopez, Park Ridge, IL (US); Mohammad Khair, Hoffman Estates, IL (US); Sanjar Ghaem, Chesapeake, VA (US); William L. Olson, Lake Villa, IL (US)

(73) Assignee: Motorola Inc., Schaumburg, IL (US)

( * ) Notice: Subject to any disclaimer, the term of this patent is extended or adjusted under 35 U.S.C. 154(b) by 0 days.

(21) Appl. No.: 09/551,718

(22) Filed: Apr. 18, 2000

(51) Int. Cl.[7] ............................................. H04B 7/005
(52) U.S. Cl. .................. 455/502; 455/426; 455/456; 600/508; 600/509
(58) Field of Search ................................ 455/426, 427, 455/9, 12.1, 13.2, 73, 456, 423; 375/219, 220; 600/508, 509; 128/903

(56) References Cited

U.S. PATENT DOCUMENTS

| | | | |
|---|---|---|---|
| 4,981,141 A | 1/1991 | Segalowitz | 128/698 |
| 5,168,874 A | 12/1992 | Segalowitz | 128/639 |
| 5,307,818 A | 5/1994 | Segalowitz | 128/696 |
| 5,511,533 A | 4/1996 | Segalowitz | 128/696 |
| 5,752,976 A * | 5/1998 | Duffin et al. | 607/32 |
| 5,862,803 A * | 1/1999 | Besson et al. | 128/903 |
| 5,930,295 A * | 7/1999 | Isley et al. | 375/219 |
| 5,957,854 A * | 9/1999 | Besson et al. | 128/903 |
| 6,032,065 A * | 2/2000 | Brown | 600/383 |
| 6,181,734 B1 * | 1/2001 | Palermo | 375/219 |
| 6,304,774 B1 * | 10/2001 | Gorman | 600/520 |

* cited by examiner

Primary Examiner—William Trost
Assistant Examiner—Congvan Tran
(74) Attorney, Agent, or Firm—Brinks Hofer Gilson & Lione

(57) ABSTRACT

A wireless, programmable system for bio-potential signal acquisition (e.g., electrocardiogram (ECG) data) includes a base unit and a plurality of individual wireless, remotely programmable transceivers that connect to patch electrodes. The base unit manages the transceivers by issuing registration, configuration, data acquisition, and transmission commands using wireless techniques. Bio-potential signals from the wireless transceivers are demultiplexed and supplied via a standard interface to a conventional monitor for display.

21 Claims, 7 Drawing Sheets

PROGRAMMABLE WIRELESS ELECTRODE SYSTEM FOR MEDICAL MONITORING

BACKGROUND OF THE INVENTION

A. Field of the Invention

This invention relates generally to the field of devices used to measure and display bio-potential signals generated by the body. More particularly, the invention relates to a plurality of wireless, remotely programmable electrode transceiver assemblies that are each coupled to a conventional patch electrode, and an associated base unit. The base unit obtains a patient's electrocardiogram (ECG) or other bio-potential signal from the wireless transceivers and supplies the signal to a monitor unit for display. The display may be a standard ECG monitor.

B. Statement of Related Art

Conventional ECG apparatus for hospital bedside monitoring typically requires up to ten wired electrodes. Each electrode is attached to the body of the patient, and has a wire, several feet or more in length, leading to an ECG monitor. Such electrodes are used to detect heart signals from the patient and convert them into a multiple-lead ECG evaluation.

The lengthy wired electrodes of conventional ECG apparatus obstruct the patient and limit the patient's freedom of movement. They are also cumbersome for the physician or assisting nurse. Telemetry systems for wireless ECG monitoring for patients in hospitals currently exist. These systems are more expensive, intended for greater range (higher power), and do not totally eliminate the physical electrode wires attached to the patient. Instead of being connected to the monitor, the electrodes are each wired to a single transmitter box that is worn by the patient. Some telemetry systems also may not handle a 12 lead ECG (10 wires) because of the wiring that is required between the electrodes and the transmitter box. For example, the Spacelabs Ultraview Modular Digital Telemetry system can only handle a maximum of four leads (5 wires).

Wireless medical monitoring and diagnosis systems have been proposed in the prior art. U.S. Pat. No. 5,862,803 to Besson et al. describes a wireless electrode/sensor patch system with sensor, controller and transceiver electronics contained in an electrode patch assembly. U.S. Pat. Nos. 5,307,818, 5,168,814 and 4,981,141, all issued to Segalowitz, describe a wireless electrode system for ECG monitoring. The Besson et al. and Segalowitz patents are incorporated by reference herein. The Segalowitz patents describe a single piece electrode patch with built-in microchips for wireless one way communication, and a snap on electronic-assembly that fastens to a disposable electrode patch. However, the electrode patch is a special two-conductor type that is not conventional. The electrode assemblies are either transmit only or receive only (not both). A reference signal (generated from a Wilson network) is transmitted from the base unit to only the Right Leg electrode patch, which is receive only. Electrodes can only be programmed via manual switches on the electrode casing, not over-the-air from the base unit. For the multiple electrode embodiment, the base unit contains multiple receivers and antennas which imply multiple transmit frequencies are required for the system and over-the-air signaling (thus making the base unit more costly to implement). There is no mention of error correction or detection capability in the electrodes or base unit.

In another embodiment of the Segalowitz '818 patent, there is discussion of a single strip assembly which contains all of the electrodes required for 12-lead ECG monitoring with microchip circuitry contained in the strip assembly (not in the individual electrode patches). In this configuration, the ECG signals from each electrode are multiplexed and transmitted from a single transmitter (contained in the strip assembly) via time multiplexing on a single digitally encoded frequency channel. However, no time multiplexing on a single frequency channel is discussed for their multiple transmit electrode embodiment, as discussed in the present invention.

The present invention is not intended to replace existing telemetry systems, but rather to provide a more convenient and cost effective solution for low power wireless ECG monitoring, in a hospital room environment, without having to replace the hospital's existing ECG bedside monitoring equipment. Furthermore, the present invention provides for programmable features by which a base unit can remotely program multiple wireless transceivers. This provides greater flexibility and customization of a wireless ECG acquisition system. As such, it is believed to be an improvement to the systems proposed by Besson et al. and Segalowitz.

SUMMARY OF THE INVENTION

In a first aspect, a wireless electrocardiogram (ECG) acquisition system is provided. The system includes a plurality of individual, remotely programmable wireless transceivers, each of which are associated with a patch electrode for use in ECG monitoring. The patch electrodes are of conventional design and adapted to be placed on the surface of the patient's body for measuring electrical potentials. The system further includes a base unit comprising a wireless transceiver for sending and receiving messages to the plurality of individual wireless transceivers. The messages include configuration commands for the plurality of individual transceivers. Examples of the configuration commands include data acquisition commands, transmission control commands, such as frequency selection commands, and other commands described in further detail below.

The base unit, in accordance with this first aspect of the invention, transmits a global time base signal to the plurality of individual wireless transceivers. The global time base signal is used for synchronizing the timing of transmission of signals acquired by the individual wireless transceivers to the base unit in discrete time slots in a single frequency channel. This time division multiplexing provides that each wireless transceiver transmits its signals to the base unit in discrete time slots, with the wireless transceivers sharing a common channel.

The base unit has an interface to an ECG monitor for display and analysis by the user. Preferably, the ECG monitor is a conventional, standard monitor typically used today in the hospital setting. The ECG signals are provided by the base unit to the monitor in a fashion that is transparent to the monitor, i.e., the data is formatted and provided in a form whereby the monitor cannot distinguish the signals from conventional, wired electrode input signals. The ECG monitor preferably accepts the individual electrode signals in order to develop any required lead configuration.

In a preferred embodiment, the wireless two-way communication between the base unit and the plurality of remotely programmable wireless transceivers is established in accordance with a protocol that provides for transmission of a variety of configuration commands. Examples of such commands include registration information, data acquisition control commands (such as start and stop messages), transmission frequency commands, time slot commands, amplifier gain commands, transmitter control commands, power saving mode commands, initialization commands, and so forth. The ability to remotely program the wireless transceivers gives considerable flexibility over how the electrodes are configured and positioned on the patient's body.

The plurality of individual wireless transceivers could be designed to be installed on particular locations of the patient's body, such as left arm, right arm, left leg, etc. In a more preferred embodiment, the individual wireless transceivers are generic with respect to particular placement locations on the surface of a patient's body. The base unit transmits programming data to the individual wireless transceivers. The programming data includes electrode position location data associated with a unique placement position to be assigned to the individual wireless transceivers, as well as electrode identification data. When the data is acquired from each of the wireless transceivers, the electrode identification data, electrode position location data and the acquired electrode signal are sent from the wireless transceivers to the base unit.

In another aspect of the invention, a dynamically programmable, wireless electrocardiograph (ECG) acquisition system is provided. The system comprises a plurality of individual, remotely programmable wireless transceivers, each transceiver associated with a patch electrode for use in ECG monitoring, and a base unit comprising a wireless transceiver for sending and receiving messages (e.g., commands) to the plurality of individual wireless transceivers. The base unit and the plurality of individual wireless transceivers implement a wireless programming protocol by which information and commands are exchanged between the base unit and individual wireless transceivers. Registration, configuration, and data transmission control properties of the individual wireless transceivers are managed dynamically by the base unit.

As an example of the information that can be transmitted between the base unit and the transceivers, the base unit may transmits a global time base signal synchronizing the timing of transmission of signals acquired by the plurality of individual wireless transceivers to the base unit in discrete time slots in a single frequency channel. Other examples include data acquisition messages, registration messages, initialization messages, frequency selection command messages, and so forth as described in further detail below.

In yet another aspect of the invention, a wireless, remotely programmable transceiver assembly is provided. The wireless transceiver assembly is adapted to attach to a patch electrode for placement on the surface of a patient's body, the assembly transmitting signals acquired from the electrode to a base unit. The electrode transceiver assembly includes an amplifier receiving a signal from the electrode and generating an amplified analog signal, a analog to digital converter converting the amplified analog signal into a digital signal, a computing platform such as a microcontroller with a Digital Signal Processor (DSP) function having a memory storing a set of instructions executable by the microcontroller/DSP, a buffer storing digital signals for transmission to the base unit and a wireless transceiver module including an antenna for wireless transmission of the digital signals to the base unit. A frequency generator is provided that is responsive to commands from the microcontroller. The frequency generator generates a signal at frequency at which the wireless transmission from the wireless transceiver assembly to the base unit is to occur. The microcontroller is operative to select a frequency for the wireless transmission in response to control commands received from the base unit.

In still another aspect of the invention, a base unit is provided for a plurality of wireless, programmable transceiver assemblies each adapted to attach to a patch electrode for placement on the surface of a patient's body. The base unit includes a transceiver module including an antenna for wireless communication in transmit and receive directions between the base unit and the wireless, programmable transceiver assemblies. The wireless communication from the wireless, programmable transceiver assemblies to the base unit occurs in a plurality of discrete time slots in a single frequency channel. The base unit further includes an encoder/decoder coupled to the antenna, a microcontroller and a memory. The microcontroller performs error correction on signals from the encoder/decoder and executes initialization and transceiver management and command routines.

The base unit further includes a demultiplexer demultiplexing received data from the plurality of wireless transceiver assemblies in the plurality of discrete time slots. A digital to analog converter converts the received, demultiplexed digital signals into analog signal. An interface supplies the analog signals to a monitor for display. Preferably, the monitor comprises a conventional, pre-existing ECG monitor. The wireless origin of the supplied analog signals is transparent to the ECG monitor.

These and still other aspects and features of the invention will be more apparent from the following detailed description of a presently preferred embodiment. In this specification, the terms "wireless transceiver" and "programmable wireless transceiver" are meant to refer to the wireless electrode transceiver assembly as a unit, as distinguished from the actual transceiver module within the assembly, unless the context clearly indicates otherwise.

BRIEF DESCRIPTION OF THE DRAWINGS

A presently preferred embodiment of the invention is described below in conjunction with the appended drawing figures, wherein like reference numerals refer to like elements in the various views, and in which.

DETAILED DESCRIPTION OF THE PREFERRED EMBODIMENT

Figure 1:
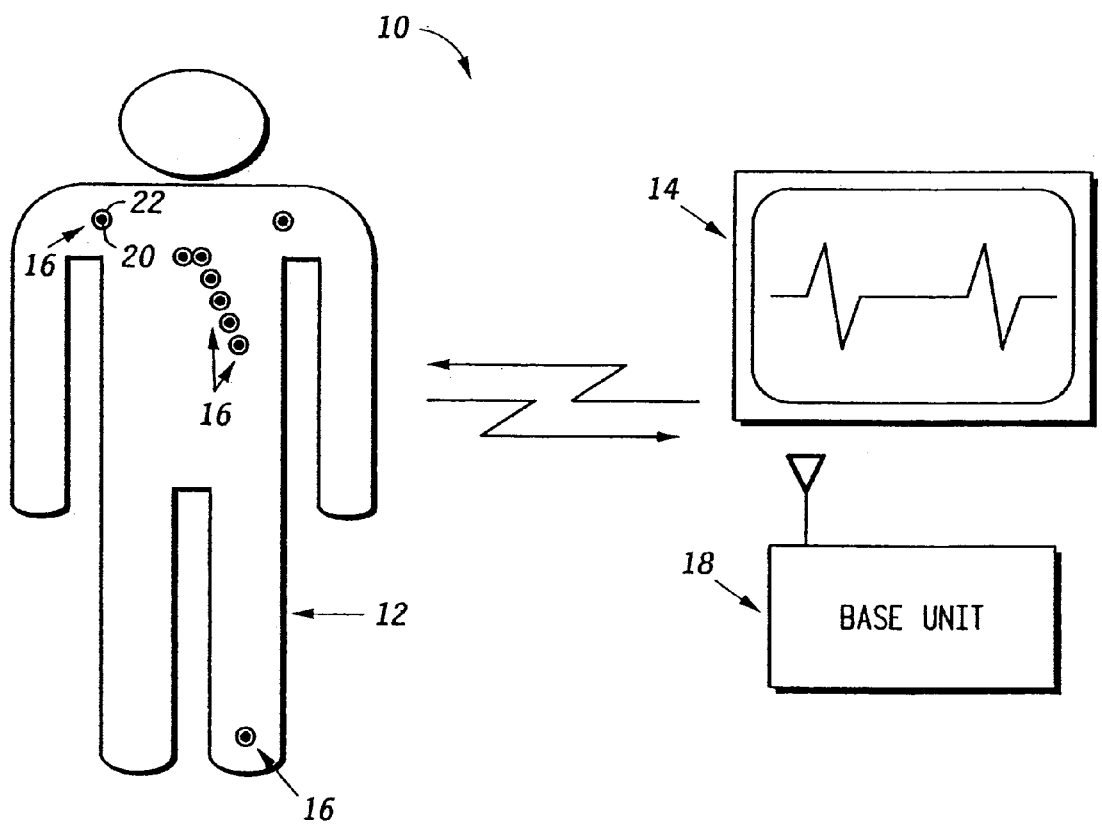
FIG. 1 is a schematic representation of the system of the present invention in use with a patient to acquire ECG signals from the patient and supply them to an ECG monitor.

The present invention provides a system consisting of multiple smart wireless transceiver devices sized to snap onto conventional disposable patch electrodes for wireless medical monitoring, and a base unit communicating with the wireless electrode devices that is also capable of interfacing to existing conventional bedside monitoring and display equipment. The system is particularly suited to wireless ECG monitoring. The electrode devices receive commands from the base unit such as registration information, transmission frequency commands, amplifier gain commands, transmitter control commands, power saving mode, etc. and include hardware and software or firmware for processing these commands and responsively configuring the wireless transceiver accordingly.

The wireless transceivers will also preferably receive a global time base signal from the base unit. The global time base signal is used for in synchronizing the timing of acquisition of sample points for all electrodes used in measuring input body surface potentials (e.g., ECG signal). The base unit receives the transmitted ECG signal from each electrode (at predetermined time intervals if time division multiplexing is the embodiment of the communication protocol), demodulates, decodes (with error correction), digitally processes the data, applies any needed signal conditioning (amplification, filtering), and converts back to analog form for outputting the ECG signals to the standard ECG equipment for display. The base unit also has a universal interface to existing standard ECG equipment so that the wireless link between the electrodes and base unit appears transparent to the ECG equipment. The ECG equipment will accept the individual electrode signals for developing any required lead configuration.

While time division multiplexing is a presently preferred embodiment for the transmission of electrode bio-potential signals, other transmission formats could be used. An example of an alternative transmission format is code division multiplexing, a technique known in the wireless communications art.

The wireless transceivers and base unit also use a unique over-the-air communication protocol between the base unit and the electrodes which allows wireless programming (configuration), identification, auditing, data acquisition control, and transmitter control of each electrode used in the ECG system. For frequency bandwidth efficiency of the invention, the system could be designed such that transmission of multi-channel ECG signals is on a single digitally encoded frequency channel between the base unit transceiver and multiple electrode devices by using time division multiplexing. For example, each electrode will receive synchronization data from the base unit on the same receive frequency, and instruction on which time slot to transmit it's digitally encoded ECG data. This makes it possible for multiple patients to use the wireless ECG system in the same hospital room if there is limited bandwidth.

Referring now to FIG. 1, a system 10 according to a presently preferred embodiment is shown schematically for use with a patient 12. The system 10 acquires ECG signals from the patient 12 and supplies them to an ECG monitor 14. The system 10 is a wireless system, in that a plurality of electrode assemblies 16 receive commands (e.g., synchronization and control commands) from a base unit 18 using wireless transmission methods, and supply the ECG signals to the base unit 18 using wireless transmission methods as well. Thus, cumbersome wires for the electrode assemblies 16 are eliminated in the illustrated embodiment.

The electrode assemblies 16 of FIG. 1 consist of a plurality of individual, remotely programmable wireless transceivers 20, each transceiver designed to snap onto a conventional patch electrode 22 (such as the 3M Red dot electrode) used in ECG monitoring. The wireless transceivers are described in further detail in conjunction with FIGS. 2 and 3. The base unit 18 includes a wireless transceiver for sending and receiving messages to the plurality of individual wireless transceivers, and is described in further detail in conjunction with FIGS. 4, 6, 8 and 9. The base unit further has an interface for providing analog ECG signals received from the wireless transceivers 20 to a conventional ECG display monitor 14.

Figure 5:
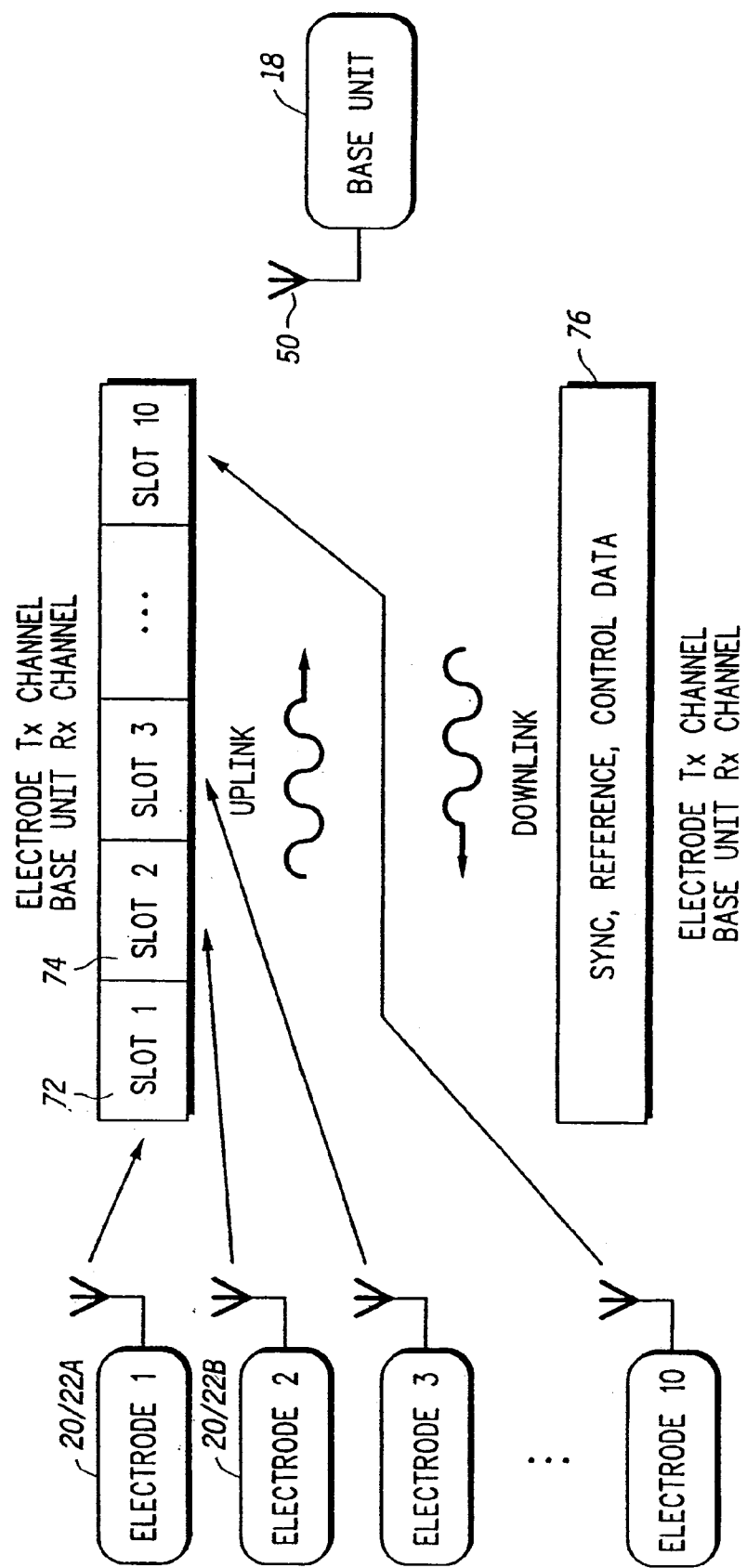
FIG. 5 is a diagram illustrating the time division multiplexing of transmission form the plurality of wireless transceivers of FIG. 1 in the uplink direction (the direction of wireless transmission from the wireless transceivers to the base unit), and the transmission of synchronization, reference and control data from the base unit to the wireless transceivers in a common channel in the downlink direction.

A preferred communications format for wireless communication between the base unit 18 and the wireless transceivers 20 is time division multiplexing in a common frequency channel in the uplink direction, that is between the transceivers and the base unit. Each wireless transceiver 20 transmits ECG signals in a particular time slot in the channel, as indicated in FIG. 5. In the downlink direction, the base unit transmits control commands and other information in a common channel that all the wireless transceivers are tuned to. The time slot assignment, frequency assignment, and other transmission control information is managed and controlled by the base unit 18, as described in further detail below. An alternative embodiment is to use code division multiple access (CDMA) communication format for wireless communication between the base unit 18 and the wireless transceivers 20, a technique known to persons skilled in the wireless digital communication art.

The messages transmitted by the base unit 18 also include configuration commands for the wireless transceivers 20. These configuration commands can be, for example, change or set the data acquisition sampling rate, amplifier gain setting, and channel carrier settings, and can also consist of a timing signal for synchronization of the transmission time slot. Preferably, the base unit 18 transmits a global time base signal to all of the wireless transceivers. The global time base signal synchronizes the timing of transmission of the ECG signals acquired by all of the wireless transceivers 20, such that the transmissions are in discrete time slots in a single frequency channel, as shown in FIG. 5.

The details of the over-the-air programming protocol to exchange messages and information between the base unit and the transceivers may be arrived at in many ways within the spirit of the present invention, and is considered within the ability of a person skilled in the pertinent art. In one possible embodiment, packets of data are transmitted between the base unit and the wireless transceivers. Particular fields in the packets (bytes of data) are reserved for control data, payload data, CRC or error correction data, etc. in accordance with known wireless transmission protocols, conventional data transmission techniques such as IP or Ethernet, or similar techniques. A presently preferred protocol is described in the application of Mohammad Khair et. al filed concurrently herewith, entitled "Wireless Protocol for Medical Monitoring", Ser. No. 09/551,719, the contents of which are incorporated by reference herein.

Figure 2:
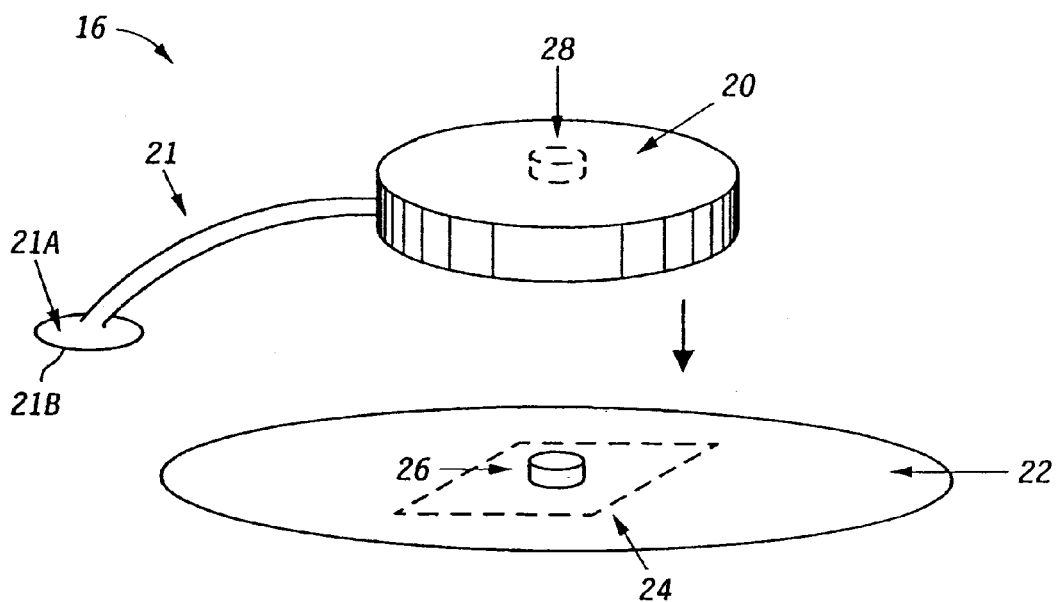
FIG. 2 is a detailed perspective view of one of the patch electrodes and associated remotely programmable wireless transceiver of FIG. 1, it being understood that all of such patch electrodes and wireless transceivers of FIG. 1 are of a construction similar to that shown in FIG. 2.

FIG. 2 is a detailed perspective view of one of the patch electrodes 22 and associated remotely programmable wireless transceiver 20 assembly 16 of FIG. 1, it being understood that all of such patch electrodes and wireless transceivers of FIG. 1 are of a construction similar to that shown in FIG. 2. The patch electrode 22 is adhered to the surface of the patient's body 12 in conventional fashion. The patch electrode 22 includes a conductor 24 supplying ECG or other signals to a pin 26. The pin 26 is received in complementary pin receiving structure 28 in the wireless transceiver 20 so as engage (as in a snap fit) the two parts 20 and 22.

The pin receiving structure 28 conducts electrical impulses with respect to a local ground reference to electronic circuitry in the wireless transceiver 20. The local ground reference consists of a flexible strip 21 connected to the transceiver 20 having a tip or skin contact 21A, made from a conductive material, which is placed underneath the patch electrode 22 in contact with the skin. The purpose is to allow the transceiver to measure the bio-potential difference between the signal contact point 26 and the local ground reference 21/21A. The material used for the strip 21 could be a thin flexible material such as plastic with an internal conductive trace or lead wire from the transceiver 20 to the skin contact point 21A. The skin contact point 21A is preferably coated with conductive silver chloride (AgCl) material 21B on one side thereof.

Figure 3:
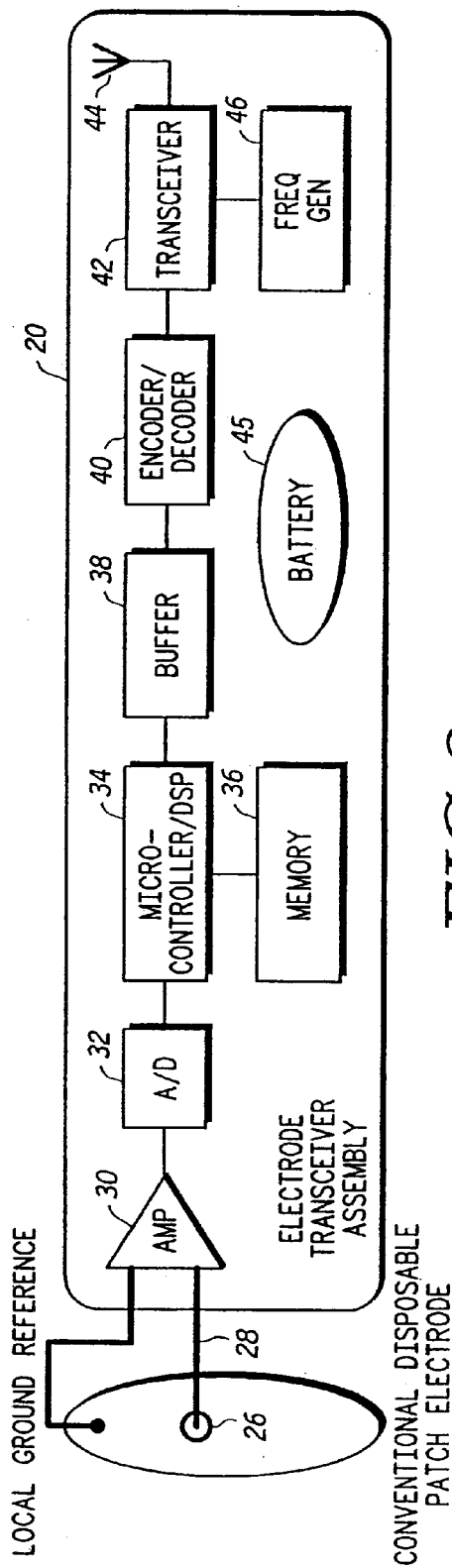
FIG. 3 is a block diagram of the wireless transceiver assembly of FIG. 2.

FIG. 3 is a block diagram of the wireless transceiver of FIGS. 1 and 2. The transceiver assembly 20 snaps onto the post pin 26 of a disposable conventional patch electrode. Electrical signals provided from the electrode 22 are supplied to a low noise, variable gain amplifier 30 in the wireless transceiver 20. The amplifier 30 may include a pre-amp stage. The analog signal is filtered, sampled and converted to digital signals in the A/D converter 32. The digital signals are supplied to a computing platform, illustrated as a microcontroller/Digital Signal Processor 34. The microcontroller performs signal processing of the digital signal supplied by the A/D converter 32. The signal processing functions include noise filtering and gain control of the digital ECG signal. In an alternative but less-preferred embodiment, gain control in the transceiver assembly could be performed by adjustment of the amplifier 30 gain in the analog signal path. The microcontroller also processes commands and messages received from the base unit, and executes firmware instructions stored in a memory 36. The memory further stores a unique electrode identifier as described in further detail below. The memory may also store a position location identifier or data associated with a position the electrode is attached to the patient. The position location identifier or data is dynamically programmable from the base unit.

The processed digital ECG signals are buffered in a buffer 38, supplied to an encoder/decoder 40 and fed to a RF transceiver module 42 for transmission to the base unit via a low power built-in RF antenna 44. The transceiver 42 includes a modulator/demodulator, transmitter, power amp, receiver, filters and an antenna switch. A frequency generator 46 generates a carrier frequency for the RF transmission. The frequency is adjustable by the microcontroller 34. A battery 45 with a negative terminal connected to a local ground reference provides DC power to the components. The microcontroller/DSP 34 controls the frequency generator 46 so as to select a frequency for wireless transmission of data and control messages to the base unit. The microcontroller in the computing platform 34 also executes an initialization routine wherein the receiver scans a default receive channel for commands from the base unit, and if the commands are received the transmitter transmits identification information in an assigned frequency and time slot to the base unit.

All or some of the individual blocks shown in FIG. 3 could be combined in a microchip or microchips to miniaturize the size of the snap-on wireless transceiver assembly 20.

Figure 4:
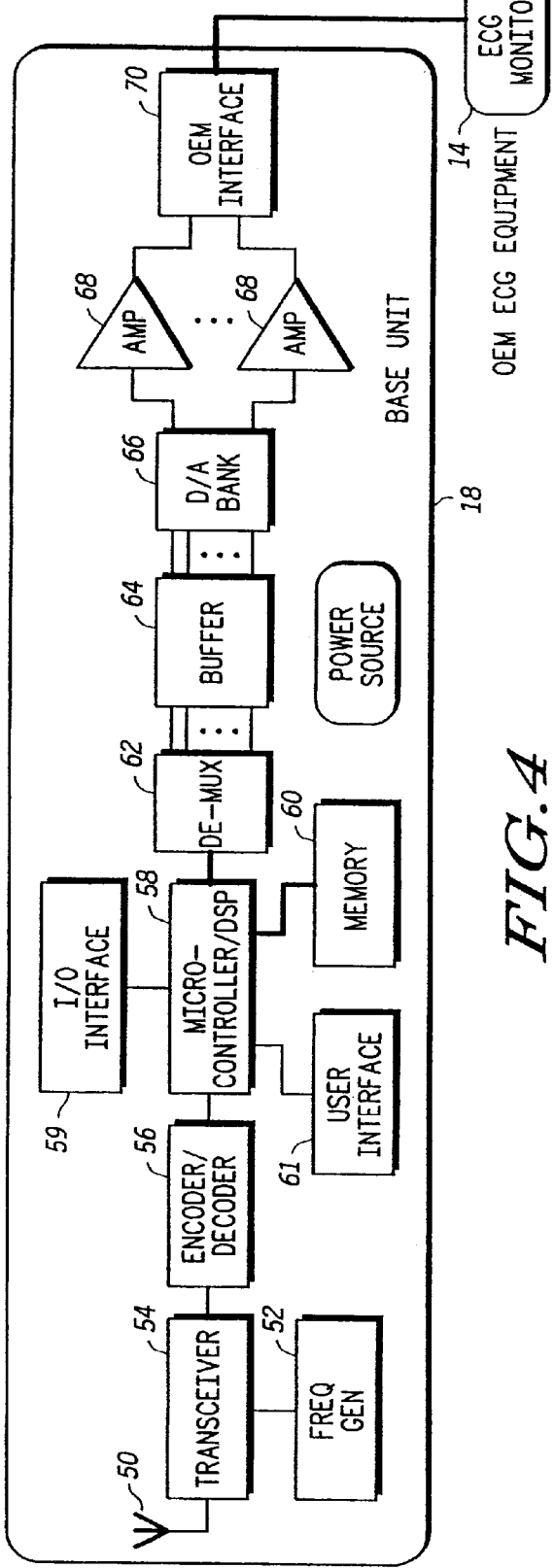
FIG. 4 is a block diagram of the base unit of FIG. 1.

Referring now to FIG. 4, the base unit 18 is shown also in block diagram form. The base unit 18 transmits commands to all of the wireless transceivers and instructs each transceiver to transmit its ECG data individually (such as in time division multiplexing). The base unit receives the transmitted ECG signals from the electrodes (up to 10) in sequence and then demodulates, decodes, error corrects, de-multiplexes, buffers, signal conditions, and reconverts each electrode's data back to an analog signal for interfacing to the standard ECG monitor 14. The base unit also transmits programming information to the electrodes for frequency selection, power control, etc.

The base unit 18 includes a low power RF antenna 50, a frequency generator 52 for generating a carrier frequency and an RF transceiver 54. The transceiver 54 includes a modulator/demodulator, transmitter, power amp, receiver, filters and an antenna switch. The base unit further includes a encoder/decoder 56, a computing platform such as a microcontroller/Digital Signal Processor (DSP) 58, and a memory 60 storing code for execution by the microcontroller/DSP, and I/O interface 59 for connection to a personal computer which is used as a test port for running system diagnostics, base unit software upgrades, etc., and a user interface 61. The user interface 61 may consist of the following: a display for indicating electrode programming information or error/alarm conditions, a keypad or buttons for user requested inputs, an alarm unit for audibly indicating error/alarm conditions (for example a detached, low battery or failed electrode), and LEDs for visually indicating error, alarm or programming status.

The time slot ECG data received from the wireless transceivers is demultiplexed in demultiplexer 62 and supplied to a buffer 64. A digital to analog filter bank 66 converts the multiple channels of digital data from the wireless transceivers to analog form. The analog signals are amplified by amplifiers 68 and supplied to an OEM (original equipment manufacturer) standard ECG monitor interface 70. The interface 70 could be either part of the base unit 18 assembly so that it can directly plug into the ECG display equipment 14 via a standard connector, or it could be part of a cable connection to the display equipment. The idea with the OEM interface 70 is to supply multiple analog ECG signals to the conventional ECG display equipment already used in the hospital environment, in a compatible and transparent manner, such that the display equipment would treat the signals as if they were generated from conventional wired electrodes. Familiarity with the analog signal acquisition hardware or electronics for the ECG display equipment 14 will be required obviously, and the OEM interface circuitry may vary depending on the manufacturer of the display equipment. The OEM monitor interface detailed design is considered within the ability of a person skilled in the art.

Referring to FIG. 5, a possible transmission scheme between the wireless transceivers 20 and the base unit 18 is time division multiplexing. This allows a single transmit frequency to be used by all the electrodes in the ECG system. All electrodes receive commands and synchronization data (time base signal, reference signal and control data 76) from the base unit 18 on an assigned receive frequency (downlink) channel. The electrode receive channel may or may not be slotted (time multiplexed). Electrode 1 20/22A transmits it's data on time slot 1 72 (Electrode 2 20/22B on time slot 2 74, etc.) at the assigned transmit frequency (uplink) channel. The base unit 18 receives the transmission from the electrodes 20/22 and demultiplexes, buffers, and reconstructs the individual electrode data.

The system 10 of FIG. 1 utilizes an over the air programming mechanism to exchange messaging and information between the base unit 18 and the wireless transceivers 20. Various types of information could be exchanged. For example, the base unit 18 transmits a data acquisition control message to the wireless transceivers, which tells the microcontroller in the wireless transceivers to start and stop data acquisition. Another command would be a frequency selection command message sent to the wireless transceivers, in which the wireless transceivers responsively select a common frequency channel for transmission of acquired ECG signals to the base unit in discrete time slots.

The following is a list of some of the possible programming commands and messages that could be sent between the base unit and the wireless transceivers:

a. Registration of electrodes 20/22 with the base unit 18. This would include the detection of the electrode type and an associated unique electrode identifier by the base unit. This could also include transmission of a unique base unit identifier to the electrodes (for example where multiple base units are within RF range of the electrodes) and detection of the base unit identifier by the electrode. Also, a patient reference number could also be stored in each electrode so it only receives commands from a specific patient-assigned base unit. Each electrode reference number is also stored in the base unit, so that data coming only from these electrodes is accepted. An additional registration feature would be assignment of a specific electrode function (i.e., position on the patient's body). This is discussed in more detail below. With each of the above commands and messages, the receiving unit would typically transmit back an acknowledgment signal indicating the receipt of the command and sending back any required information to the transmitting unit.
b. Configuration of data acquisition sampling rate.
c. Configuration of amplifier 30 gain setting.
d. Configuration of preamplifier filter band settings.
e. Configuration of carrier channel settings, namely the frequency of the carrier signal generated by the frequency generator 46 in the transceivers.
f. Configuration of timing signal for transmission time slot. This needs to be synchronized with the data acquisition rate.
g. Battery 45 utilization sleep/activation mode.
h. Battery 45 low voltage level detection.
i. Data acquisition start/stop scenario.
j. Data transmit procedure.
k. Error sample data recover/retransmit scenario.
l. System test diagnostic procedure
m. Scan of electrode current channel setting procedure
n. Electrode detection procedure.
o. Electrode status audit.
p. Base unit status audit.
q. Data acquisition subsystem audit.

In a preferred embodiment, for every smart wireless transceiver, the system will provide a registration mechanism whereby an electrode identifier is dynamically programmed into the base unit. Additionally, the electrode functional position on the patent (i.e., LA, RA, LL, V1, V2, V3, V4, V5, or V6) is dynamically assigned. An Electrode Universal Identifier (EUI) will encode the smart electrode unique serial number. During data transaction, each electrode is assigned a temporary identifier after each registration scenario (on power up or reconfiguration). The temporary identifier can be composed of electrode number and random number for example.

Electrode System Initialization

Figure 6:
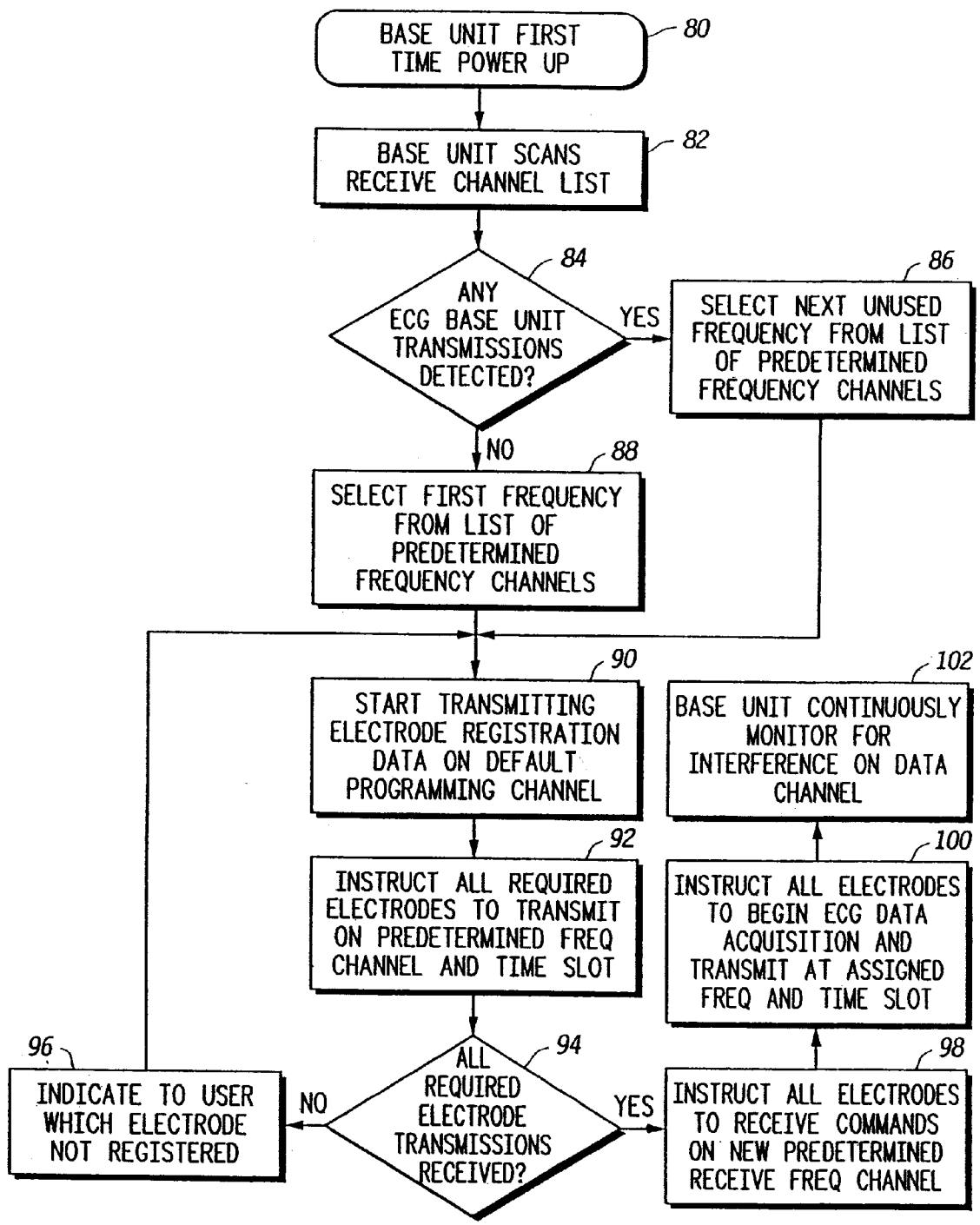
FIG. 6 is a flow diagram illustrating a base unit initialization routine.

FIG. 6 shows a flow diagram of a possible initialization procedure (for both the base unit 18 and electrodes 20/22) for use where the transmission scheme between the base unit and the wireless transceivers 20 is time division multiplexing. This procedure assumes that each electrode in the ECG system contains a unique identifier and a unique functional position ID (i.e., LA, RA, LL, V1, V2, V3, V4, V5, or V6).

Figure 9:
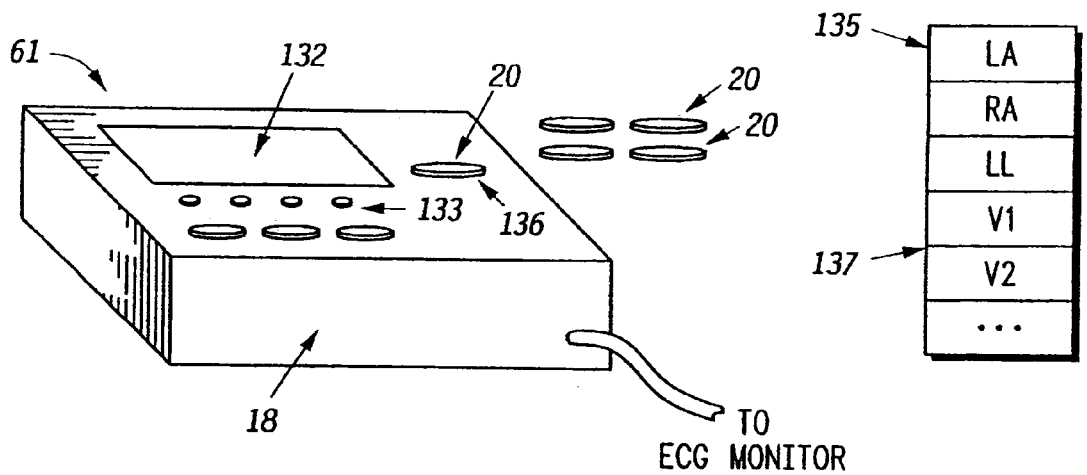
FIG. 9 is a perspective view of a base unit of FIG. 4 and a group of wireless transceivers being initialized according to the procedure of FIG. 8.

At step 80, the base unit is powered up. The base unit is configured for the number of leads used in the ECG system, such as 3, 5 or 12. The configuration could be facilitated by means of any suitable user interface on the base unit 18, such as a display and buttons as shown in FIG. 9 and described subsequently. At step 82, the base unit scans its receive channels, a list of which is programmed into the base unit. At step 84, the base unit determines whether any other ECG base unit transmissions are detected. If so, at step 86 the base unit selects the next unused frequency from the list of predetermined frequency channels as a transmit channel. If not, at step 88 the base unit selects the first frequency from the list of predetermined frequency channels as the transmission channel. The process then proceeds to step 90.

At step 90, the base unit stars transmitting electrode registration data and messages on the default programming channel determined in steps 86 or 88. The registration data and messages include a base unit identification code or serial number. The registration data and messages were described earlier. This insures that the wireless transceivers to be associated with this particular base unit being initialized respond to commands from this base unit and no other base unit. At step 92, the base unit instructs all required electrodes to transmit on a predetermined frequency channel, and assigns time slots to each electrode. The base unit then communicates with electrodes to complete registration. If a particular electrode or electrodes did not complete registration, the base unit indicates via its user interface which electrode is not registered at step 96. If registration is completed for all the electrodes, the base units instruct all electrodes to receive commands on a new predetermined frequency channel at step 98. At step 100, the base unit instructs all electrodes to begin ECG data acquisition and to transmit at the assigned frequency and in the assigned time slot. Step 100 may be started in response to a user prompt via the base unit user interface. During data acquisition, at step 102 the base unit continuously monitors for interference on the receive data channel (uplink direction). If excessive interference occurs (such as from a high bit error rate detected in the base unit microcontroller), the base unit selects a new channel from the list of available frequencies for the electrodes to transmit on and commands a change in transmit frequency.

Figure 7:
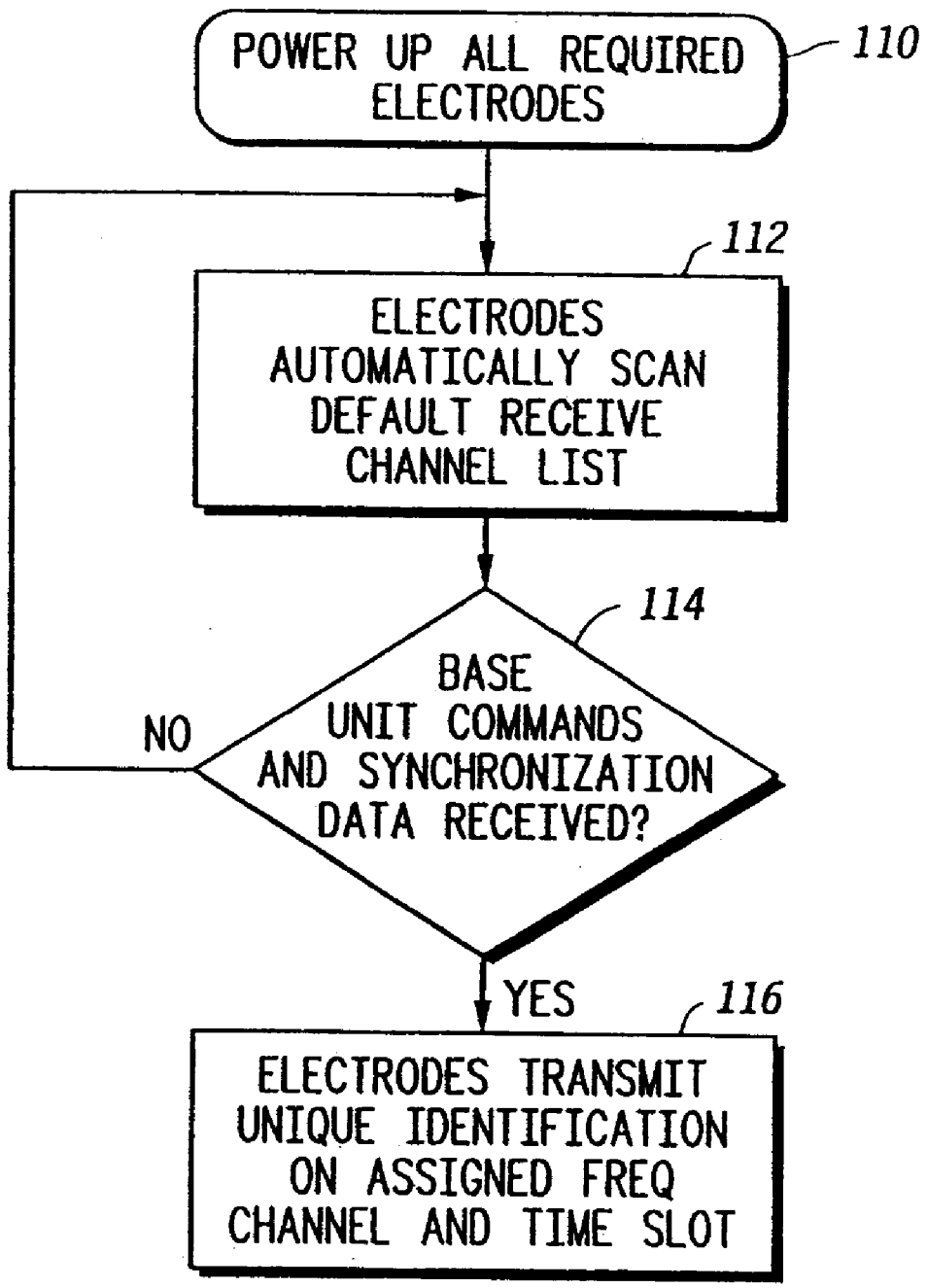
FIG. 7 is a flow diagram illustrating a wireless transceiver initialization routine.

FIG. 7 is a flow diagram of an electrode initialization procedure that may be employed. When the electrodes are initially powered up at step 110, the electrodes will be in a receive only mode. At step 112, the electrodes automatically scan the default receive channel to see if any commands and synchronization signals are being transmitted by the base unit. If no commands and synchronization commands are received at step 114, the electrode goes back to step 112 and selects another receive frequency from its list of default frequencies. If commands and synchronization data have been received, at step 116 the electrode sends is unique identification data (containing information on the position on the patient's body) on the assigned frequency and in the assigned time slot back to the base unit, indicating to the base unit that it is ready to acquire ECG signals and is in an operating condition.

In an alternative embodiment of the invention, the plurality of individual, remotely programmable wireless transceivers 20 are initially generic with respect to particular placement locations on the surface of a patient's body. Furthermore, the electrodes could be manufactured without preprogrammed functional position identifiers. This is advantageous since it would not be necessary to have the hospital or user maintain an inventory of individual electrodes based on functional position (i.e., LA, RA, LL, V1, V2, etc.). All the electrode assemblies are considered generic and could be programmed with unique identifiers indicating the position on the body by the base unit when the user sets up the ECG system. The procedure of FIG. 8 could be used for programming of each electrode when initializing the ECG system. After first time programming of the electrode assemblies, the system only needs to go through the initialization program of FIG. 6 when it is powered up again.

Figure 8:
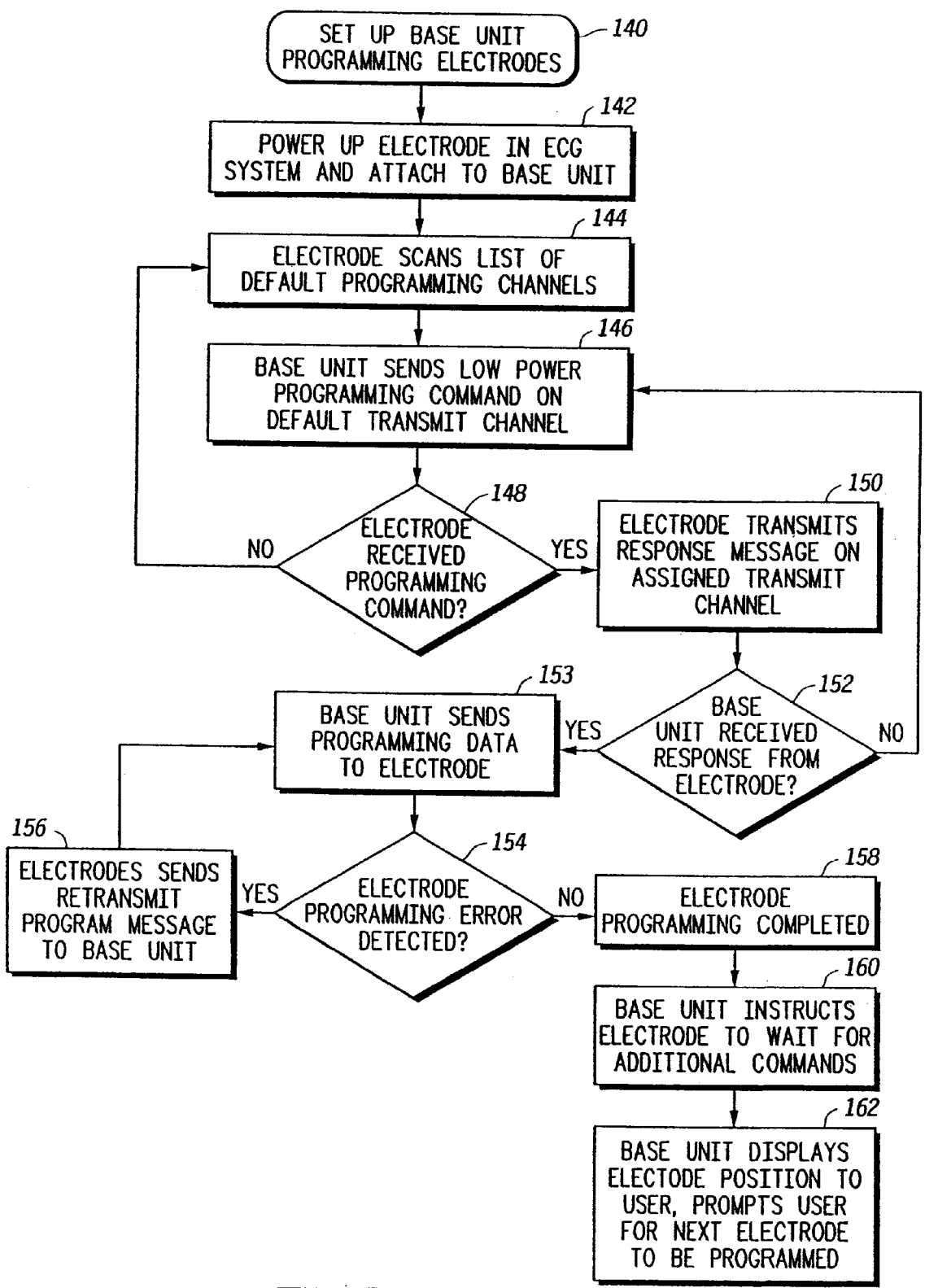
FIG. 8 is a flow diagram of a programming procedure for programming the wireless transceivers of FIG. 1 when initializing the ECG system of FIG. 1.
Figure 10:
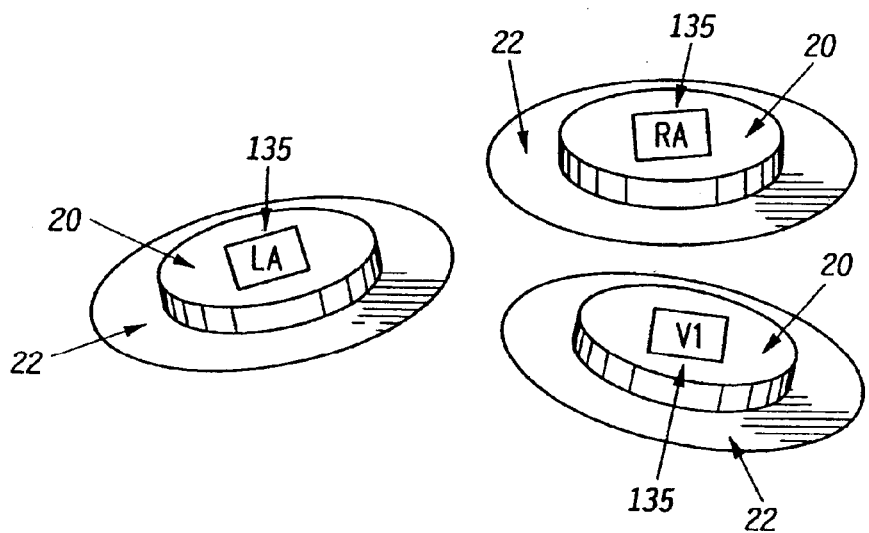
FIG. 10 is a perspective view of three wireless transmitters after the procedure of FIG. 8 has been completed.

FIG. 8 shows the initialization procedure in the alternative embodiment. FIG. 9 shows the base unit 18 having a user interface 61 comprising a display 132 and a plurality of buttons or keys 133 for assisting the user to interact with the base unit. A group of generic wireless transceivers 20 are shown ready for initialization. The user has a set of preprinted labels 135, which are removed from a plastic backing and placed on the wireless transceivers as shown in FIG. 10.

Referring now to FIGS. 8 and 9, at step 140 the user sets up the base unit into an electrode programming mode, such as by responding to prompts on the display 132 and selecting the mode with one of the buttons or keys 133. The base unit programming mode could be done at lower power transmissions, requiring the wireless transceiver 20 to be programmed to be adjacent to the base unit (thereby avoiding programming more than one transceiver at a time). Alternatively, as shown in FIG. 9, the base unit has a programming initialization interface 136 which makes contact with a socket or other feature in the transceiver for purposes of programming the transceiver during initialization. When the transceiver is placed into contact with the programming initialization interface 136, the base unit could automatically go into programming mode, or it could simply go into programming mode upon power up.

In any event, at step 142 the first electrode assembly 20/22 is powered up and placed near the base unit or positioned in contact with the programming initialization interface 136. The initialization of the electrodes could be done by mechanical means, such as plugging the electrode transceiver 20 into the base unit programming initialization interface 136.

At step 144, the electrode scans the default programming channel. At step 146, the base unit sends a low power programming command on the default transmit channel or some other channel that has the least RF interference. At step 148, the electrode determines whether it has received the programming command. If not, the electrode scans the list of default channels and selects a new channel to listen on. If so, the electrode transmits a response message on its assigned transmit channel at step 150. At step 152, the base unit determines whether it has received the response from the electrode. If not, the base unit goes back to step 146 and transmits the low power programming command on a new transmit channel. If so, the base unit transmits programming data to the electrode at step 153. At step 153, the programming data includes the electrode unique identifier, including the electrode position (LA, RL, or V3, etc.), the base unit unique identifier, and other registration commands as described above. At step 154, the electrode determines whether a programming error was detected, and if so at step 156 sends a retransmit program message to base unit causing it to repeat the programming data at step 152. If no error occurred, the process proceeds to step 158, at which the electrode completes programming with the base unit. At step 160, the base unit instructs the electrode to wait for additional commands. At this point, since the unique base unit ID has been programmed in the wireless transceiver, it can scan ECG system control channels and receive and operate on commands only from the base unit that programmed the transceiver. At step 162, the base unit displays the electrode placement position on the user interface display and prompts the user to place the next electrode for programming into the initialization interface 136.

After all the electrodes have been programmed, the base unit will automatically be configured for the proper number of electrodes used in the ECG system. As each electrode is programmed the user removes a label 135 from the stock of labels 137 indicating the position programmed on the electrode and applies the label to the electrode (e.g., to the top or upper surface of the wireless transceiver 20), as shown in FIG. 10.

From the foregoing description, it will appreciated that we have described a dynamically programmable, wireless biopotential signal acquisition system, comprising: a plurality of individual, remotely programmable wireless transceivers 20, each transceiver associated with a patch electrode 22 for use in medical monitoring, and a base unit 18 comprising a wireless transceiver 54 (FIG. 4) for sending and receiving messages to the plurality of individual transceivers 20. The base unit and wireless transceivers 22 implement a wireless programming protocol by which messages and information are exchanged between base unit 18 and wireless transceivers 20 (such as shown in FIGS. 6 and 8) whereby registration, configuration, and data transmission control properties of the wireless transceivers may be managed by the base unit.

Preferably, the base unit transmits a global time base signal to the wireless transceivers, the global time base signal synchronizing the timing of transmission of bioppotential signals acquired by the wireless transceivers in discrete time slots in a single frequency channel. As shown in FIGS. 1 and 4, the base unit further comprises an interface 70 to a conventional ECG monitoring equipment such as a display, whereby acquired ECG signals may be transmitted to the ECG monitoring equipment for display. The system of base unit 18 and wireless remotely programmable transceivers 20 is particularly well adapted for use with standard conventional patch electrodes and existing ECG monitoring equipment, and thus presents a flexible, low cost and convenient system for acquiring ECG signals and presenting them to a display unit for display.

Persons skilled in the art will appreciate that the details of the presently preferred embodiment described herein can be changed and modified without departure from the spirit and scope of the invention. The system can be used to acquire ECG signals, electroencephalogram signals, electromyography signals, or other types of signals. This true spirit and scope is to be determined in reference to the appended claims.

We claim:

1. A wireless bio-potential signal acquisition system, comprising:

a) a plurality of individual, remotely programmable wireless transceivers, each of said transceivers associated with a patch electrode for use in medical monitoring, and b) a base unit comprising a wireless transceiver for sending and receiving messages to said plurality of individual, remotely programmable wireless transceivers, said messages including configuration commands for said plurality of individual, programmable wireless transceivers;

said base unit transmitting a global time base signal to said plurality of individual, remotely programmable wireless transceivers, said global time base signal for synchronizing the timing of transmission of signals acquired by said plurality of individual, programmable wireless transceivers to said base unit in discrete time slots in a single frequency channel, said base unit further comprising an interface to a monitor, whereby said acquired signals may be sent from said base unit to said monitor for display; and wherein said plurality of individual, remotely programmable wireless transceivers are generic with respect to particular placement locations on the surface of a patient's body, and wherein said base unit transmits programming commands to said individual, remotely programmable wireless transceivers, said programming commands including electrode position location data associated with a unique placement position for said individual, remotely programmable wireless transceivers and electrode identification data.

2. The system of claim 1, wherein said base unit transmits a data acquisition control message(s) to said plurality of individual, remotely programmable wireless transceivers.

3. The system of claim 1, wherein said base unit transmits a frequency selection command message(s) to said plurality of individual, remotely programmable wireless transceivers, said plurality of individual, remotely programmable wireless transceivers responsively selecting a common frequency channel for transmission of said acquired signals to said base unit in said discrete time slots.

4. The system of claim 1, wherein said base unit further comprises a display, and wherein said unique placement position for said individual, remotely programmable wireless transceivers is displayed on said display to a user.

5. The system of claim 1, wherein said individual, remotely programmable wireless transceivers transmit response message(s) to said base unit in response to said programming commands.

6. The system of claim 1, wherein said system is used to acquire ECG signals.

7. The system of claim 1, wherein said system is used to acquire electroencephalogram signals.

8. The system of claim 1, wherein said system is used to acquire electromyography signals.

9. A wireless bio-potential signal acquisition system, comprising:

a) a plurality of individual, remotely programmable wireless transceivers, each of said transceivers associated with a patch electrode for use in medical monitoring, and b) a base unit comprising a wireless transceiver for sending and receiving messages to said plurality of individual, remotely programmable wireless transceivers, said messages including configuration commands for said plurality of individual, programmable wireless transceivers;

said base unit transmitting a global time base signal to said plurality of individual, remotely programmable wireless transceivers, said global time base signal for synchronizing the timing of transmission of signals acquired by said plurality of individual, programmable wireless transceivers to said base unit in discrete time slots in a single frequency channel, said base unit further comprising an interface to a monitor, whereby said acquired signals may be sent from said base unit to said monitor for display;

wherein said base unit transmits a frequency selection command message(s) to said plurality of individual, remotely programmable wireless transceivers, said plurality of individual, remotely programmable wireless transceivers responsively selecting a common frequency channel for transmission of said acquired signals to said base unit in said discrete time slots; and wherein said individual, remotely programmable wireless transceivers store a list of available, predetermined frequency channels for transmission of said acquired signals to said base unit and wherein said frequency selection command message(s) commands said plurality of individual, remotely programmable wireless transceivers to transmit said acquired signals to said base unit on one of said predetermined frequency channels.

10. A dynamically programmable, wireless bio-potential signal acquisition system, comprising:

a) a plurality of individual, remotely programmable wireless transceivers, each of said transceivers associated with a patch electrode for use in medical monitoring, and b) a base unit comprising a wireless transceiver for sending and receiving messages to said plurality of individual, remotely programmable wireless transceivers, c) wherein said base unit and said plurality of individual, programmable wireless transceivers implement a wireless programming protocol by which said messages are exchanged between said base unit and said plurality of individual, remotely programmable wireless transceivers whereby registration, configuration, data acquisition control, and data transmission control properties of said plurality of individual, remotely programmable wireless transceivers may be managed by said base unit;

wherein the base unit further comprises an interface to monitoring equipment, the base unit operable to output data on the interface formatted as electrode input signals.

11. The system of claim 10, wherein said base unit transmits a global time base signal to said plurality of individual, remotely programmable wireless transceivers, said global time base signal for synchronizing the timing of transmission of signals acquired by said plurality of individual, programmable wireless transceivers to said base unit in discrete time slots in a single frequency channel.

12. The system of claim 10, wherein said base unit further comprises the interface to conventional monitoring and display equipment, whereby said acquired signals may be sent from said base unit to said monitoring and display equipment for display.

13. The system of claim 10, wherein said base unit transmits a frequency selection command message(s) to said plurality of individual, remotely programmable wireless transceivers, said plurality of individual, remotely programmable wireless transceivers responsively selecting a common frequency channel for transmission of acquired signals to said base unit in discrete time slots.

14. The system of claim 10, wherein said system is used to acquire ECG signals.

15. The system of claim 10, wherein said system is used to acquire electroencephalogram signals.

16. The system of claim 10, wherein said system is used to acquire electromyography signals.

17. The system of claim 10, wherein said wireless transceivers communicate with said base unit in a Code Division Multiple Access (CDMA) communication format.

18. A dynamically programmable, wireless bio-potential signal acquisition system, comprising:
   a) a plurality of individual, remotely programmable wireless transceivers, each of said transceivers associated with a patch electrode for use in medical monitoring, and
   b) a base unit comprising a wireless transceiver for sending and receiving messages to said plurality of individual, remotely programmable wireless transceivers,
   c) wherein said base unit and said plurality of individual, programmable wireless transceivers implement a wireless programming protocol by which said messages are exchanged between said base unit and said plurality of individual, remotely programmable wireless transceivers whereby registration, configuration, data acquisition control, and data transmission control properties of said plurality of individual, remotely programmable wireless transceivers may be managed by said base unit; and
   wherein said plurality of individual, remotely programmable wireless transceivers are generic with respect to particular placement locations on the surface of a patient's body, and wherein said base unit transmits programming data to said individual, remotely programmable wireless transceivers, said programming data including electrode position location data associated with a unique placement position for said individual, remotely programmable wireless transceivers and electrode identifier data.

19. The system of claim 18, wherein said base unit further comprises a display, and wherein said unique placement position for said individual, remotely programmable wireless transceivers is displayed on said display to a user.

20. The apparatus of claim 19, wherein said computing platform includes a digital signal processor.

21. A dynamically programmable, wireless bio-potential signal acquisition system, comprising:
   a) a plurality of individual, remotely programmable wireless transceivers, each of said transceivers associated with a patch electrode for use in medical monitoring, and
   b) a base unit comprising a wireless transceiver for sending and receiving messages to said plurality of individual, remotely programmable wireless transceivers,
   c) wherein said base unit and said plurality of individual, programmable wireless transceivers implement a wireless programming protocol by which said messages are exchanged between said base unit and said plurality of individual, remotely programmable wireless transceivers whereby registration, configuration, data acquisition control, and data transmission control properties of said plurality of individual, remotely programmable wireless transceivers may be managed by said base unit;
   wherein said base unit transmits a frequency selection command message(s) to said plurality of individual, remotely programmable wireless transceivers, said plurality of individual, remotely programmable wireless transceivers responsively selecting a common frequency channel for transmission of acquired signals to said base unit in discrete time slots; and
   wherein said individual, remotely programmable wireless transceivers store a list of available, predetermined frequency channels for transmission of said acquired signals to said base unit and wherein said frequency selection command message(s) commands said plurality of individual, remotely programmable wireless transceivers to transmit said acquired signals to said base unit on one of said predetermined frequency channels.

* * * * *